United States Patent
Doi et al.

(10) Patent No.: US 6,660,771 B1
(45) Date of Patent: Dec. 9, 2003

(54) REMEDIES FOR LIVER REGENERATION OF TRANSPLANTED LIVER

(75) Inventors: Hideyuki Doi, Miyagi (JP); Hiromichi Komatsu, Miyagi (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 86 days.

(21) Appl. No.: 10/069,365

(22) PCT Filed: Aug. 23, 2000

(86) PCT No.: PCT/JP00/05637

§ 371 (c)(1), (2), (4) Date: Feb. 25, 2002

(87) PCT Pub. No.: WO01/13912

PCT Pub. Date: Mar. 1, 2001

(30) Foreign Application Priority Data

Aug. 23, 1999 (JP) ............................ 11-235283

(51) Int. Cl.⁷ ............................... A61K 31/195
(52) U.S. Cl. ........................................ 514/561
(58) Field of Search ........................... 514/561

(56) References Cited

U.S. PATENT DOCUMENTS 5,580,903 A   12/1996   Mawatari et al.

FOREIGN PATENT DOCUMENTS

| EP | 0 769 295 A1 | 4/1997 |
| WO | WO 99/16433 A1 | 4/1999 |

OTHER PUBLICATIONS

K. Urata et al., "Calculation of Child and Adult Standard Liver Volume for Liver Transplantation", *Hepatology*, May 1995, vol. 21, pp. 1317–1321.

J.C. Emond et al., "Function Analysis of Grafts from Living Donors", *Annals of Surgery*, Oct. 1996, vol. 224, No. 4, pp. 544–554.

S. Kawasaki et al., "Living Related Liver Transplantation in Adults", *Annals of Surgery*, Feb. 1998, vol. 227, No. 2, pp. 269–274.

H. Uchiyama et al., "Effects of Deletion Variant of Hepatocyte Growth Factor on Reduced–Size Liver Transplantation in Rats", *Transplantation*, Jul. 15, 1999, vol. 68, No. 1, pp. 39–44.

B. Saint–Aubert et al., "Influence of Nutrition on Liver Regeneration", in *New Aspects of Clinical Nutrition*, Kleinberger et al., eds., 1983, pp. 548–557.

P. Rigotti et al., "Effects of Amino Acid Infusions on Liver Regeneration after Partial Hepatectomy in the Rat", *Journal of Parenteral and Enteral Nutrition*, 1986, vol. 10, No. 1, pp. 17–20.

M. Holecek et al., "Effect of Branched Chain Amino Acids on Liver Regeneration After Partial Hapatectomy", *Physiologia Bohemoslovaca*, 1985, vol. 34, pp. 359–366.

*Primary Examiner*—James H Reamer
(74) *Attorney, Agent, or Firm*—Browdy and Neimark, P.L.L.C.

(57) ABSTRACT

An object of the present invention is to provide a drug that can promote liver regeneration after partial liver transplantation and rapidly induce liver regeneration even for small grafts. According to the present invention, therapeutic liver-regenerating agents for liver transplants, containing valine as an active ingredient are provided.

18 Claims, No Drawings

REMEDIES FOR LIVER REGENERATION OF TRANSPLANTED LIVER

TECHNICAL FIELD

The present invention relates to therapeutic liver-regenerating agents for liver transplants, containing valine as an active ingredient. It also relates to hepatocyte growth promoters for liver transplants.

BACKGROUND ART

Hepatic failure is a terminal picture of many liver diseases and is treated by liver transplantation, but a lack of donor organs is becoming a worldwide problem. Living donor partial liver transplantation is recognized as a measure for overcoming the lack of organs, and facilities for partial liver transplantation are increasing in the United States and European countries having advanced transplantation technology. However, partial liver transplantation cannot be considered a safe operation for adults representing the majority of transplantation patients because the resectable liver weight of donors is often less than the necessary liver weight for recipients. Thus, there is a demand for a means for safe and rapid liver regeneration for small grafts.

Conventional medical protocols for safe partial liver transplantation involve calculating the normal liver volume of the patient from the body surface area and examining and evaluating the percentage of the graft to be transplanted to the normal liver volume. Examination of the graft weight/normal liver volume ratio and postoperative hepatic function tests showed that the lower limit of the graft volume should be about 30% of the normal liver volume, and therefore, larger grafts are generally used for adult living donor partial liver transplantation (Hepatology, 21, 1317 (1995); Ann. Surg., 224, 544 (1996); Ann. Surg. 227, 269 (1998)).

Factors or drugs having a liver-regenerating effect have been known. Hepatocyte growth factor (HGF) is now under study and development as a potential drug for promoting liver regeneration. The liver-regenerating effect of HGF on liver transplants was recently reported (Transplantation, 68, 39 (1999)).

It was also reported that the so-called amino acid blend transfusion formulations have a liver-regenerating effect after hepatic resection (Kleinberger G, Deutsch E, eds. "New aspects of clinical nutrition. Basel", karger, 548–557 (1983); JPEN., 10, 17–20 (1986); Physiol Bohemoslov., 34, 359–366 (1985).

Japanese Laid-open Patent Publication No. 8-067628 describes a therapeutic liver-regenerating agent containing valine as an active ingredient. This document describes that valine has a liver-regenerating effect after partial liver resection.

However, until now it has not been known that valine has a liver-regenerating effect on liver transplants; nor has it been known that valine promotes hepatocyte growth of liver transplants or promotes improvement, recovery or normalization of hepatic functions of liver transplants.

DISCLOSURE OF THE INVENTION

An object of the present invention is to provide a drug that can promote liver regeneration or hepatocyte growth after liver transplantation such as partial liver transplantation. Another object of the present invention is to provide a drug that can safely promote liver regeneration or hepatocyte growth even for small grafts. Still another object of the present invention is to provide a drug that can safely promote rapid liver regeneration or hepatocyte growth after liver transplantation.

As a result of careful studies to achieve the above objects, the present inventors accomplished the present invention on the basis of the finding that remarkable liver regeneration is observed when valine is administered to rats having received partial liver transplantation.

Accordingly, the present invention provides a therapeutic liver-regenerating agent for a liver transplant, containing valine as an active ingredient. The present invention also provides a therapeutic liver-regenerating agent after liver transplantation, containing valine as an active ingredient.

The present invention also provides a hepatocyte growth promoter for a liver transplant, containing valine as an active ingredient., The present invention also provides said therapeutic liver-regenerating agent or hepatocyte growth promoter, which promotes improvement, recovery or normalization of hepatic functions of the liver transplant.

BEST MODE FOR CARRYING OUT THE INVENTION

The present application claims priority based on Japanese Laid-open Patent Publication No. 11-235283, the disclosure of which is wholly incorporated herein as reference.

Valine used in the present invention may be commercially available or synthesized or prepared by any process. It may be in any of D-, L- and DL-configurations, but preferably L-configuration.

In the present invention, the term "liver transplantation" has the common meaning in the art and includes partial and whole liver transplantations in which the liver of a donor is partially or wholly resected and partially or wholly transplanted into a recipient. Partial liver transplantation is classified by operation mode into orthotopic partial liver transplantation, heterotopic partial liver transplantation and the like, and the present invention can be applied to any of them. In partial liver transplantation, a liver transplant or a partial liver transplant from a donor corresponding to about 30–50% of the normal liver volume of a recipient is typically transplanted as a graft into the recipient whose liver has been wholly resected, but the present invention has the effect of promoting liver regeneration or hepatocyte growth even if the graft is about 30% or less.

As used herein, "liver transplant" means a liver transplanted into a recipient by the transplantation operation as described above, and also includes the so-called "partial liver transplant" corresponding to a graft consisting of a part of the liver of a donor.

As used herein, "liver regeneration" after liver transplantation means morphologic changes in which lost liver tissues are replaced by hepatocyte growth of a liver transplant or partial liver transplant, but also includes biochemical changes such as improvement, recovery or normalization of hepatic functions.

The preferred administration route is normally intravenous, but oral, enteral and the like administrations are also suitable. Valine used in the present invention can be applied alone as a formulation exclusively containing it, but preferably is combined with a transfusion formulation such as an intravenous hyperalimentation formulation containing glucose or the like or added to a transfusion formulation.

Suitable dosage forms include solutions, suspensions, emulsions, tablets, capsules, granules, fine granules, powders, suppositories, etc. These dosage forms are preferably prepared with pharmaceutically acceptable liquid or solid additives such as excipients, fillers, extenders, solvents, emulsifiers, lubricants, flavoring agents, perfumes, dyes, buffering agents, etc.

The dose depends on the sex, body type, constitution, age and condition of the patient and the dosage form used, but can be appropriately chosen at a valine level of 0.5–10.0%, preferably 0.5–5.0% in the case of transfusion formulations such as amino acid transfusion formulations to be administered from peripheral veins or central veins, or 0.5–10.0% in the case of ampules or vials to be added to transfusions, or 5.0–100% in the case of other dosage forms for oral or enteral administration such as suspensions, emulsions, tablets, capsules, granules, fine granules, powders, suppositories, etc.

Administration can be started at any time after liver transplantation. The administration period need not be long because a rapid liver-regenerating effect can be expected from the present invention, normally after administration for 5 days at a minimum, but preferably 7–10 days.

Specific subjects to be treated include, for example, patients who received partial liver transplantation after the liver had been wholly resected for treating hepatic failure caused by liver diseases such as hepatitis, hepatic cirrhosis of alcoholic, viral, drug or unknown cause or hepatic cancer.

As used herein, "%" representing valine levels means w/v % when valine is liquid or w/w % when valine is solid.

EXAMPLES

The following examples further illustrate the present invention without, however, limiting the invention thereto.

Example 1
Liver Regeneration-promoting Effect of L-valine in Rat Partial Liver Transplantation Male Wistar rats at 8 weeks of age (240–280g; 8–9 animals per group) were used for 30% orthotopic partial liver transplantation.

Isolation of the liver from donors was performed as follows. Animals were abdominally incised under ether anesthesia and about 70% of the liver was resected and the common bile duct and arteries were separated immediately before starting liver perfusion with cold physiological saline from the portal vein. After starting perfusion, the remaining liver with the portal vein and the posterior vena cava-was removed from the donor animal.

Recipients were abdominally incised under Nembutal anesthesia and the whole liver was resected and the upper end of the posterior vena cava of the graft was continuously sutured (7-0 proline) with the proximal end of the posterior vena cava of the recipients. The donor posterior vena cava of the graft was sutured end-to-end with that of the recipient, and the portal vein and common bile duct of the graft were anastomosed with those of the recipient, respectively, by the cuff technique.

The operation period was 45 minutes on average, the anhepatic period was within 900 seconds, and the total period for cold-storing the graft was 1 hour.

Immediately after the operation was completed, a catheter was inserted from the jugular vein. The catheter was passed through the subcutaneous tunnel across both scapulae, and connected to a swivel through a protective coil after a harness was put on the animal. Rats were transferred to a metabolic cage and divided into the following two groups and continuously pumped with the transfusion formula at an administration rate of 50 ml/kg/day up to day 5.

Valine group: An aqueous solution of L-valine (Japanese Pharmacopoeia) at 3.376% was transfused in combination with glucose at 5% on the day of operation and 20% on days 1–5.

Control group: A solution of a 10% amino acid blend formula (Moripron F® made by Roussel Morishita Co., Ltd.) diluted in distilled water at a total nitrogen level equivalent to that of the valine group was transfused in combination with glucose at 5% on the day of operation and 20% on days 1–5.

Animals were given free access to normal feed and water.

On day 5, animals were abdominally incised under ether anesthesia and blood was collected from the abdominal aorta and the liver was separated after bleeding. Serum protein (TP), albumin (ALB), GOT, GPT and LDH and the liver weight were determined. The resected liver was fixed with formalin to prepare a hematoxylin-eosin stained sample for histological tests.

The measurement results were expressed in mean±SD and statistically analyzed by the Mann-Whitney U test to show a significant difference if $p<0.05$. Liver weight gain and relative liver gain were determined as morphologic indications of the liver-regenerating effect. Here, the liver weight gain means (liver weight on day 5)–(liver weight on day 0), and the relative liver gain means (liver weight on day 5)/(liver weight on day 0). Not the liver weight itself but the liver weight gain was chosen as indication because liver transplants vary in weight and the difference between the weight of each liver transplant (weight on day 0) and the weight of the regenerated transplant (weight on day 5) more appropriately indicates changes in the transplant.

The measurement results are shown in Table 1.

TABLE 1

| Group | Liver weight (g) on day 0 | Liver weight (g) on day 5 | Liver weight gain (g) | Relative liver gain |
|---|---|---|---|---|
| Control group (n = 9) | 3.31 ± 0.36 | 6.18 ± 0.70 | 2.87 ± 0.88 | 1.89 ± 0.31 |
| Valine group (n = 8) | 3.16 ± 0.45 | 7.05 ± 0.99 | 3.88 ± 0.66* | 2.24 ± 0.18* |

(Liver weight gain) = (Liver weight on day 5) − (Liver weight on day 0)
(Relative liver gain) = (Liver weight on day 5) / (Liver weight on day 0)
*p < 0.05.

The liver weight gains in valine group and control group were 3.88±0.66 g and 2.87±0.88 g, respectively, and the respective relative liver gains were 2.24±0.18 and 1.89±0.31, showing that both were significantly higher in valine group ($p<0.05$).

No significant difference was found during biochemical blood tests. No abnormal observation was found in each individual during histopathological tests of the regenerated liver. Neither control group nor valine group showed edema or necrosis of hepatocytes.

INDUSTRIAL APPLICABILITY

According to the present invention, liver regeneration or hepatocyte growth after liver transplantation such as partial liver transplantation can be safely promoted. Also according to the present invention, liver regeneration or hepatocyte growth can be safely promoted even for small grafts. Also according to the present invention, safe operations and early postoperative recovery can be ensured by rapid liver-regenerating effect or hepatocyte growth effect after liver transplantation.

What is claimed is:

1. A method for regenerating a liver transplant, comprising administering to a subject in need thereof an amount of valine effective to regenerate the liver transplant.

2. The method of claim 1 wherein the liver transplant is a partial liver transplant.

3. The method of claim 1 wherein the valine is L-valine.

4. The method of claim 1, wherein the valine is administered as a transfusion formulation.

5. The method of claim 4 wherein the valine level is 0.5–10.0%.

6. The method of claim 5 wherein the valine level is 0.5–5.0%.

7. The method of claim 1, wherein the valine is administered for 7–10 days.

8. A method for regenerating a liver after liver transplantation, comprising administering to a subject in need thereof an amount of valine effective to regenerate the liver.

9. The method of claim 8 wherein the liver transplantation is a partial liver transplantation.

10. The method of claim 8 wherein the valine is L-valine.

11. The method of claim 8, wherein the valine is administered as a transfusion formulation.

12. The method of claim 11 wherein the valine level is 0.5–10.0%.

13. The method of claim 12 wherein the valine level is 0.5–5.0%.

14. The method of claim 8, wherein the valine is administered for 7–10 days.

15. A method for promoting hepatocyte growth for a liver transplant, comprising administering to a subject in need thereof an amount of valine effective to promote hepatocyte growth for the liver transplant.

16. The method of claim 15 wherein the liver transplant is a partial liver transplant.

17. The method of claim 15 or 16, wherein said amount is an amount sufficient to further promote improvement, recovery or normalization of hepatic functions.

18. The method of claim 15, wherein the valine is administered for 7–10 days.

* * * * *